(12) United States Patent
Wang et al.

(10) Patent No.: US 6,956,009 B2
(45) Date of Patent: Oct. 18, 2005

(54) MICROPHASE SEPARATED SUPERABSORBENT COMPOSITIONS AND METHOD FOR MAKING

(75) Inventors: James Hongxue Wang, Appleton, WI (US); Jayant Chakravarty, Appleton, WI (US); Thomas Kremer, Appleton, WI (US); David Glen Biggs, Neenah, WI (US); Xiaomin Zhang, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 128 days.

(21) Appl. No.: 10/722,802

(22) Filed: Nov. 26, 2003

(65) Prior Publication Data

US 2004/0116287 A1 Jun. 17, 2004

Related U.S. Application Data

(62) Division of application No. 10/036,841, filed on Dec. 21, 2001, now Pat. No. 6,861,477.

(51) Int. Cl.$^7$ ................................................ B01J 20/00
(52) U.S. Cl. ........................ 502/400; 502/401; 502/402
(58) Field of Search ................................. 502/400, 401, 502/402, 526; 252/184

(56) References Cited

U.S. PATENT DOCUMENTS

| | | | |
|---|---|---|---|
| 3,650,995 A | 3/1972 | Erickson | |
| 3,663,462 A | 5/1972 | Arndt et al. | |
| 3,887,408 A | 6/1975 | Hoey | |
| 3,901,240 A | 8/1975 | Hoey | |
| 3,992,333 A | 11/1976 | Emmons et al. | |
| 4,000,028 A | 12/1976 | Hoey | |
| 4,069,366 A | 1/1978 | Hoey | |
| 4,071,650 A | 1/1978 | Gross | |
| 4,117,184 A | 9/1978 | Erickson et al. | |
| 4,318,408 A | 3/1982 | Korpman | |
| 4,394,930 A | 7/1983 | Korpman | |
| 4,415,388 A | 11/1983 | Korpman | |
| 4,449,977 A | 5/1984 | Korpman | |
| 4,486,489 A | 12/1984 | George | |
| RE31,822 E | 2/1985 | Erickson et al. | |
| 4,649,164 A | 3/1987 | Scott et al. | |
| 4,685,909 A | 8/1987 | Berg et al. | |
| 4,818,600 A | 4/1989 | Braun et al. | |
| 4,820,773 A | 4/1989 | Alexander et al. | |
| 4,861,539 A | 8/1989 | Allen et al. | |
| 4,902,565 A | 2/1990 | Brook | |
| 4,959,060 A | 9/1990 | Shimomura et al. | |
| 5,015,245 A | 5/1991 | Noda | |
| 5,071,681 A | 12/1991 | Manning et al. | |
| 5,102,597 A | 4/1992 | Roe et al. | |
| 5,124,188 A | 6/1992 | Roe et al. | |
| 5,128,087 A | 7/1992 | Slocum et al. | |
| 5,139,841 A | 8/1992 | Makoui et al. | |
| 5,147,345 A | 9/1992 | Young et al. | |
| 5,268,224 A | 12/1993 | DesMarais et al. | |
| 5,318,554 A | 6/1994 | Young et al. | |
| 5,324,561 A | 6/1994 | Rezai et al. | |
| 5,328,935 A | 7/1994 | Van Phan et al. | |
| 5,331,015 A | 7/1994 | DesMarais et al. | |
| 5,338,766 A | 8/1994 | Phan et al. | |
| 5,346,485 A | 9/1994 | Yarbrough et al. | |
| 5,364,382 A | 11/1994 | Latimer et al. | |
| 5,372,766 A | 12/1994 | Roe | |
| 5,378,528 A | 1/1995 | Makoui | |
| 5,387,207 A | 2/1995 | Dyer et al. | |
| 5,428,076 A | 6/1995 | Roe | |
| 5,451,353 A | 9/1995 | Rezai et al. | |
| 5,451,452 A | 9/1995 | Phan et al. | |
| 5,490,846 A | 2/1996 | Ellis et al. | |
| 5,506,035 A | 4/1996 | Van Phan et al. | |
| 5,508,381 A | 4/1996 | Jang et al. | |
| 5,536,264 A | 7/1996 | Hsueh et al. | |
| 5,562,646 A | 10/1996 | Goldman et al. | |
| 5,563,179 A | 10/1996 | Stone et al. | |
| 5,571,849 A | 11/1996 | DesMarais | |
| 5,632,737 A | 5/1997 | Stone et al. | |
| 5,650,222 A | 7/1997 | DesMarais et al. | |
| 5,692,939 A | 12/1997 | DesMarais | |
| 5,713,881 A | 2/1998 | Rezai et al. | |
| 5,728,081 A | 3/1998 | Baer et al. | |
| 5,741,581 A | 4/1998 | DesMarais et al. | |
| 5,744,506 A | 4/1998 | Goldman et al. | |
| 5,760,080 A | 6/1998 | Wada et al. | |
| 5,763,067 A | 6/1998 | Brüggemann et al. | |
| 5,763,499 A | 6/1998 | DesMarais | |
| 5,786,395 A | 7/1998 | Stone et al. | |
| 5,797,893 A | 8/1998 | Wada et al. | |
| 5,849,805 A | 12/1998 | Dyer | |
| 5,851,648 A | 12/1998 | Stone et al. | |
| 5,856,370 A | 1/1999 | Chmelir | |
| 5,859,074 A | 1/1999 | Rezai et al. | |
| 5,868,724 A | 2/1999 | Dierckes, Jr. et al. | |
| 5,904,675 A | 5/1999 | Laux et al. | |

FOREIGN PATENT DOCUMENTS

| | | |
|---|---|---|
| CA | 884608 | 11/1971 |
| EP | 311 344 | 4/1989 |
| JP | 106 178 | 4/1988 |
| JP | 106 713 | 4/1988 |
| WO | 94/28839 | 12/1994 |
| WO | WO 98/32906 | 7/1998 |
| WO | WO 99/11728 | 3/1999 |
| WO | WO 00/05448 | 2/2000 |

*Primary Examiner*—Edward M. Johnson
(74) *Attorney, Agent, or Firm*—Pauley Petersen & Erickson

(57) ABSTRACT

A superabsorbent composition comprising a superabsorbent material and an elastomer. The superabsorbent composition has a two-phase morphology resulting in one of the superabsorbent material and elastomer being dispersed as aggregates in the other continuous material. The superabsorbent composition has a low glass transition temperature. The low glass transition temperature gives the superabsorbent composition many beneficial properties. This invention also discloses novel superabsorbent particles, fibers, films, and microporous films. Also disclosed in this invention are personal care articles comprising such particles, fibers, films and microporous films.

37 Claims, 11 Drawing Sheets

I 1 mm

I1 mm

I1 mm

I1 mm

MICROPHASE SEPARATED SUPERABSORBENT COMPOSITIONS AND METHOD FOR MAKING

CROSS REFERENCE TO RELATED APPLICATION

This application is a divisional application of U.S. application, Ser. No. 10/036,841, filed on 21 Dec. 2001, now U.S. Pat. No. 6,861,477. The co-pending parent application is hereby incorporated by reference herein in its entirety and is made a part hereof, including but not limited to those portions which specifically appear hereinafter.

FIELD OF THE INVENTION

This invention relates to a superabsorbent composition having a dispersed elastomer which has a low glass transition temperature. The dispersed elastomer is beneficial in that it increases elasticity, softness, and creates macropores in a superabsorbent film to increase fluid transfer.

BACKGROUND OF THE INVENTION

Superabsorbent particles and fluff are used in disposable personal care products such as diapers and training pants. Current commercial superabsorbents are typically comprised of a single polymer such as, for example, neutralized polyacrylic acid, hydrolyzed starch-acrylonitrile graft polymer, partially neutralized starch-acrylonitrile graft polymer, and saponified vinyl acetate-acrylic ester copolymers. Although current commercial superabsorbent particles and fluff provide the necessary absorbency, they typically have a glass transition temperature above room temperature. Superabsorbent compositions with an above room temperature glass transition temperature are rigid and brittle at room temperature, the typical temperature of use.

Rigid and brittle superabsorbent compositions are problematic for numerous reasons. During diaper production rigid superabsorbent particles are prone to poke through the surrounding carrier tissue layer and can cause abrasion damage to the polyolefin outer cover films, rendering the diaper unfit for use or sale. Also brittle superabsorbent particles can fragment during production leading to dust or fragment penetration of the inner lining during use.

In addition to the above problems, superabsorbent particles are not bonded in current commercial composites and the superabsorbent is therefore mobile. This mobility can cause a change in the distribution of the superabsorbent during the assembling process or during shipping prior to use. The resulting disposable personal care products will not provide the desired absorbency and may result in leakage.

Interparticle bonded aggregates of superabsorbent particles have been developed to solve the problem of superabsorbent particles mobility. Such aggregate macrostructures are disclosed in Roe et al., U.S. Pat. No. 5,102,597, and Rezai et al., U.S. Pat. No. 5,324,561. Although bonded superabsorbent particle aggregates decreases mobility of the particles, this solution results in undesired surface non-uniformity and a lengthy production process. Another solution, disclosed in Allen et al., U.S. Pat. No. 4,861,539, is to cast a superabsorbent precursor into a film which is subsequently crosslinked to form a solid superabsorbent film. This solution also has its deficiencies in that the film is nonporous and has poor liquid transport properties and is prone to gel-blocking.

There is a need or desire in the industry to create a softer, less brittle superabsorbent composite and a superabsorbent film that has good liquid transport properties that is not prone to gel-blocking.

SUMMARY OF THE INVENTION

The present invention is directed to a superabsorbent composition comprising a superabsorbent component and an elastomer. The differences in polarity and composition between the superabsorbent component and the elastomer cause a two-phase morphology in the superabsorbent composition. The two-phase morphology results in one component, the component of less percent by weight, being dispersed as aggregates in the other component, which serves as a continuous or semi-continuous matrix.

Superabsorbent materials typically have a higher than room temperature glass transition temperature resulting in rigid and brittle superabsorbent compositions. The elastomer of this invention has a low glass transition temperature. A superabsorbent composition having an elastomer results in the superabsorbent composition having a low glass transmission temperature. The resulting superabsorbent composition is softer, more flexible, more durable, and has other beneficial properties useful in personal care absorbent articles and protective garments.

In one embodiment of this invention the elastomer is in a composition range of about 10%–30% by weight. In this range the aggregating elastomer causes formation of macropores during the film making process. The macropores allow for better fluid transfer through the superabsorbent film and still retain the absorbency of the superabsorbent component. Macroporous superabsorbent films also are beneficial when used in personal care absorbent articles and protective garments.

The two-phase superabsorbent compositions of this invention are beneficial in that they can result in thinner, more lightweight personal care absorbent articles and protective garments.

The foregoing and other features and advantages will become further apparent from the following detailed description of the presently preferred embodiments read in conjunction with the drawings.

DEFINITIONS

Figure 1:
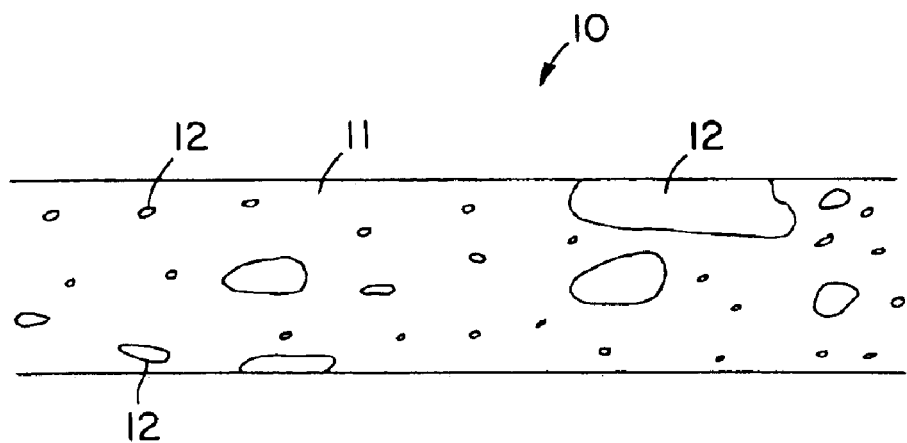
FIG. 1 is a cross-sectional view of a film having a two-phase distribution according to one embodiment of the invention.

Within the context of this specification, each term or phrase below will include the following meaning or meanings.

The term "film" refers to an extremely thin continuous sheet of a substrate that may or may not be in contact with another substrate. Film may be made using thermoplastic polymer by a film extrusion process, such as a cast film or blown film extrusion process or a solution casting process from a polymer solution.

The term "macroporous film" refers to a film having large pores visible to the naked eye and having a diameter as high as several millimeters. As the pores are not generally perfect circles the diameter is measured by the equivalent circular diameter. The pores of a macroporous film can have varying sizes. The pores permit the flow of liquids.

The term "elastomeric" refers to a material or composite which can be elongated by at least 50 percent of its relaxed length and which will recover, upon release of the applied force, at least 40 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

The term "polymer" includes, but is not limited to, homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to isotactic, syndiotactic and atactic symmetries.

The term "superabsorbent component" refers to a water-swellable, water-insoluble organic or inorganic material capable, under the most favorable conditions, of absorbing at least about 10 times its weight, preferably at least about 15 times its weight in an aqueous solution containing 0.9% by weight sodium chloride.

The term "dispersed phase" refers to the component morphology of the superabsorbent composite component having the lesser percentage by weight. In the dispersed phase, the dispersed phase component is in unconnected, isolate individual particles or aggregates of varying size. The dispersed phase represent the "islands" in an "islands-in-the-sea" morphology because of the dispersed phase component aggregations in the continuous phase.

The term "continuous phase" refers to the morphology of the component having the greater percentage by weight. The continuous phase is generally continually connected and substantially engulfs the dispersed phase component. The continuous phase represents the "sea" in what is referred to as an "islands-in-the-sea" morphology.

The term "islands-in-the-sea" refers to the morphology of the dispersed phase in the continuous phase. The dispersed aggregates of the dispersed phase component make up isolated "islands" in the "sea" of the continuous phase component.

The term "absorbent article" includes without limitation diapers, training pants, swim wear, absorbent underpants, baby wipes, adult incontinence products, feminine hygiene products, facial tissues, and paper towels.

The term "protective garment" includes without limitation medical garments, underpads, bandages, absorbent drapes, and medical wipes, as well as industrial work wear garments.

These terms may be defined with additional language in the remaining portions of the specification.

DETAILED DESCRIPTION OF THE PRESENTLY PREFERRED EMBODIMENTS

FIG. 1 shows an embodiment of a superabsorbent composition as a superabsorbent film 10. The superabsorbent composition preferably has a low glass transition temperature. The low glass transition temperature superabsorbent composition of this invention results from having a two-phase superabsorbent composition. The first phase comprises a superabsorbent component 11 and the second phase comprises an elastomer 12 having a low glass transition temperature.

Superabsorbent component 11 comprises a superabsorbent precursor. In one embodiment the superabsorbent precursor is a linear neutralized polyacrylic acid. "Linear" means the polyacrylic acid precursor is substantially unbranched in structure. "Neutralized" means that the carboxyl acid groups of the precursor molecule are neutralized to their salt equivalents using a base such as sodium hydroxide, sodium carbonate, or other hydroxide. "Partially neutralized" means only a specific mole fraction of the carboxylic acid groups in the superabsorbent precursor is neutralized. Suitable partially neutralized polyacrylic acid is 40% to 90% neutralized, more suitably 45% to 85% neutralized, and most suitably 50% to 80% neutralized.

The polyacrylic acid superabsorbent precursor solution can contain a linear polyacrylic acid with latent nonpolymerizable crosslinker or a copolymer of acrylic acid and a polymerizable latent crosslinking compound such as aminopropyl vinyl ether, ethylene glycol vinyl ether, or combinations thereof. Possible latent nonpolymerizable crosslinkers include, without limitation, α,β-ethylenically unsaturated comonomers having an additional functional group including, for example, hydroxy, amino, and epoxy groups. Examples of latent polymerizable crosslinkers include, without limitation, ethylene glycol allyl ether, 2-hydroxyethyl methacrylate, polyethylene glycol methacrylate, ethylene glycol vinyl ether, and aminopropyl vinyl ether. Nonpolymerizable latent crosslinkers are compounds containing two or more functional groups capable of reacting with carboxyl groups. Examples of such functional groups include amino, hydroxy, epoxy, etc. Examples of latent nonpolymerizable crosslinkers include, without limitation, polyfunctional alcohols, polyfunctional amines, polyfunctional alcohols and amines on the same molecule, and mixtures thereof. Examples of latent nonpolymerizable crosslinkers include, without limitation, ethylene glycol, diethylene glycol, 1,1,1-trimethylolpropane, 1,4-butanediol, 1,4-butanediamine, 1,5-pentanediamine, 1,6-hexanediamine, or any chemical having functional groups that react with carboxylic acid groups, such as amino, hydroxy, and epoxy groups.

Other superabsorbent materials include, without limitation hydrolyzed starch-acrylonitrile graft copolymers, partially neutralized starch-acrylonitrile graft copolymers, partially neutralized saponified vinyl acetate acryl-ester copolymers, hydrolyzed acronitrile copolymers, carboxymethyl cellulose, carboxymethyl starch, chitosan salts, partially neutralized polyaspartic acid, polyquarternary ammonium salts, polyvinyl amines, polyvinyl imines, and combinations thereof.

Superabsorbent component 11 can comprise two or more superabsorbent precursors. When used in combination the ratio of the first superabsorbent precursor to the second superabsorbent precursor can be about 99:1 to 1:99. Suitably the range of the ratio of the first superabsorbent precursor to the second superabsorbent precursor is about 90:10 to 10:90, and most suitably about 80:20 to 20:80. The advantages of using two superabsorbent precursors in combination include providing complimentary absorbent properties, complementary liquid wicking properties, and other desirable properties.

In one embodiment a second superabsorbent precursor is a copolymer of an α-olefin with one of an α,β-ethylenically unsaturated organic acid anhydride and ester. The α-olefin monomer can have from 3 to 20 carbon atoms, and in one embodiment the preferred α-olefin monomer is isobutylene. Other suitable α-olefin monomers include propylene, 2-methyl 1-butene, 2-ethyl 1-butene, 2,4 dimethyl pentene, and any olefins with electron donating groups such as alkyl, cycloalkyl, amino, alkoxy groups, etc. The α,β-ethylenically unsaturated acids include, but are not limited to, fumaric acid and esters and maleic anhydride and esters. A preferred copolymer is a hydrolyzed copolymer of isobutylene and maleic anhydride. Such a copolymer is available from Kuraray America, Inc. (New York, N.Y.) under the trade name ISOBAM™. ISOBAM™ can be hydrolyzed by adding ISOBAM™ powder to water with the addition of an aqueous alkaline solution such as sodium hydroxide, potassium hydroxide, ammonium hydroxide, or other alkaline solutions for about 4 to 5 hours at about 80° C. to 100° C.

A nonpolymerizable latent crosslinker can be added to the neutralized ISOBAM™ solution. Possible nonpolymerizable latent crosslinkers include polyols, polyamines, or polyepoxy compounds. Examples include, without limitation, ethylene glycol, diethylene glycol, triethylene glycol, polyethelene glycol, polyvinyl alcohol, polyethylele oxide, glycerol, 1,3-propanediol, 1,4-butanediol, 1,5-pentanediol, 1,6-hexanediol, 1,8-octanediol, 1,1,1-trimethylolpropane, 1,4-butanediamine, 1,5-pentanediamine, 1,6-hexanediamine, diethylenetriamine, and analogs and derivatives thereof. Crosslinking density in the resulting superabsorbent composition is determined by the amount of polyfunctional compound present. Most specifically, the crosslinking density is determined by the ratio of the moles of the functional groups in the latent crosslinkers to the moles of the carboxylic acid in the superabsorbent precursor polymer. The higher the ratio, the higher the crosslinking density. As the crosslinking density is increased, key absorbency properties such as absorbency under load, gel stiffness, gel bed permeability, etc. are also increased.

The amount of crosslinkable component preferably ranges from about 0.5% to about 15% by weight. Higher amounts of crosslinking components usually leads to higher crosslinking density, higher gel stiffness, and a lower molecular weight ($M_c$) between the crosslinks. More preferably the crosslinking component is in a range from about 1% to about 8% by weight. Most preferably the crosslinking component is in a range from about 2% to about 6% by weight. The concentration of the copolymer in water is preferably in the range of about 15% to about 50%. Viscosity of the solution depends upon the molecular weight of the polymer in solution. Using a higher concentration of a lower molecular weight polymer will result in a suitable solution for film preparation, and reduce the drying time needed.

Unlike current commercial superabsorbents based on copolymerized neutralized polyacrylic acid, crosslinking of the superabsorbent composition of this invention occurs after production of the superabsorbent precursor composition (i.e., after the film is produced). Crosslinking of the superabsorbent precursor polymers can be done by heat curing. Alternative crosslinking methods include exposing the polymers to microwaves or electron beam radiation. These alternative methods are much quicker than heat curing and can also be performed continuously.

Various elastomers can be used in the second phase of superabsorbent composition 10, including latex emulsions, liquid rubbers, and ground fine particles of elastomers with sizes ranging from 1 to 20 microns. The embodiment of FIG. 1 comprises an elastomer derived from a latex emulsion. The latex emulsion can be a polymerized copolymer emulsion of various combinations of acrylic monomers, acrylamide, and olefinic monomers. Examples of preferred monomers include, without limitation, alkyl acrylate, vinyl acetate, acrylonitrile, acrylic acid, styrene, and butadiene. Other latex components can also be used. The presence of water in the latex emulsion make it easier to disperse the elastomer particles in the superabsorbent material.

Superabsorbent compositions typically have high glass transition temperatures. Where superabsorbent polymers have a glass transition temperature higher than room temperature (about 25° C.), the typical temperature of product use, the superabsorbent polymer is rigid, hard, and brittle. The typical glass transition temperature of superabsorbent material is about 100° C., which is why at 25° C. the superabsorbent material is brittle. These characteristics lead to a large amount of dust during production and the superabsorbent material piercing the lining of a disposable wearable absorbent article. By adding an elastomer with a lower glass transition temperature to the high glass transition temperature superabsorbent component to create a two-phase superabsorbent composition, the undesired characteristics are reduced or eliminated.

The superabsorbent precursor solution can contain more than one superabsorbent precursor. For example, the superabsorbent precursor solution can comprise a combination of a first precursor such as partially hydrolyzed copolymer of isobutylene and maleic acid and a second precursor such as partially neutralized polyacrylic acid. When the superabsorbent precursor solution contains more than one superabsorbent precursor the first and second precursors can be in a ration of about 99:1 or 1:99, more suitably of about 90:10 to 10:90, and more suitably of about 80:20 to 20:80.

The process for making superabsorbent films, fibers, and particle of the composite of this invention involves high intensity mixing of the superabsorbent precursor solution and a latex solution. Additives, such as plasticizers, antioxidants, and light stabilizers, may also be added. Examples of plasticizers include polar polyfunctional compounds such as glycerol, ethylene glycol, and oligomers such as polyethylene glycols and the alkyl ethers of polyethylene glycols. Antioxidants and light stabilizers prevent oxidation during processing and use.

Mixing can be accomplished by various devices including a high intensity stirred mixing tank, a kneader, a batch mixer, a blender, and single or multi-screw extruders. Heated mixing devices can be used to reduce viscosity of the solution.

Figure 13:
FIG. 13 is a photograph of a comparative superabsorbent particle.
Figure 14:
FIG. 14 is a photograph of a superabsorbent fiber according to one embodiment of this invention.

The mixed solutions of superabsorbent precursors can contain one of the latent crosslinkers and when the solution is dried under heat and adequate ventilation yields a solid. This solid can be ground into particles ranging in size from about 50 to 1000 microns, and more suitable from about 150 to 800 microns. The ground particles are cured under crosslinking conditions of at least about 120° C. to 200° C. to produce a superabsorbent particle with an elastomer dispersed within. FIG. 13 shows comparative superabsorbent particles that do not have an elastomer component as taught in this invention. FIG. 14 shows superabsorbent particles that do have elastomer as taught in this invention.

Figure 15:
FIG. 15 is a photograph of a superabsorbent particle according to one embodiment of this invention.
Figure 16:
FIG. 16 is a photograph of a superabsorbent fiber according to one embodiment of this invention.

Superabsorbent particles, films, and fibers can be made from any superabsorbent precursor solutions of this invention. FIGS. 15 and 16 are photographs of superabsorbent fibers according to this invention. FIG. 15 is a photograph of a superabsorbent fibers with 10% by weight of elastomer based on the total weight of the elastomer and the superabsorbent. FIG. 16 is a photograph of a superabsorbent fibers with 30% by weight of elastomer based on the total weight of the elastomer and the superabsorbent. Fibers are made by putting the precursor solutions into any known fiber spinning apparatus, such as a solution spinning process. The fiber is then dried overnight at about 60° C., a higher temperature can also be used for a shorter time. In a continuous fiber spinning process, the fiber can be dried continuously in an oven or by heated air. The fiber is then crosslinked in an oven at about 120° C. for about 4 hours, 180° C. for 0.5 hour, or other suitable temperature/time combinations, to obtain fibers with dispersed elastomeric particles. The fibers typically have a diameter of about 0.1 microns to 100 microns, or about 1 micron to 70 microns, or about 5 microns to 50 microns. The elastomer allows for a softer, less brittle fiber because of the lower glass transition temperature. Films can be made in a similar manner as fibers using a film extruder instead of the fiber spinning apparatus.

Superabsorbent compositions of this invention are useful in absorbent articles and can provide many benefits over present commercial superabsorbent composites. Superabsorbent compositions of this invention generally allow production of thinner absorbent articles and generally do not exhibit as much dust during production or use as typical current commercial superabsorbent composites. Also, the superabsorbent compositions of this invention are less rigid and softer than current commercial superabsorbent materials and do not poke through the absorbent composite liners of absorbent articles. Superabsorbent compositions, such as films or fibers, with a low glass transition temperature exhibit the desired softness, toughness, and flexibility. Preferably the glass transition temperature of elastomer 12 is less than 25° C., more preferably the glass transition temperature is less than 0° C., and most preferably the glass transition temperature is −25° C. or less.

As disclosed above, the latex solution can comprise various combinations of comonomers. Preferable comonomers include vinyl acetate and acrylic ester copolymers, ethylene vinyl acetate copolymers, styrene butadiene copolymers, and polyacrylonitriles. Two styrene-butadiene copolymer latex emulsions used in development were manufactured by BFGoodrich (Cleveland, Ohio). GOOD-RITE® SB1168 is a styrene-co-butadiene emulsion having a solid content of 52% by weight, bound styrene at 45%, and a glass transition temperature of −25° C. HYCAR® 1581 is a carboxy-modified butadiene-acrylonitrile emulsion having a solid content of 46% by weight and a glass transition temperature of −16° C.

FIG. 1 shows an embodiment of a superabsorbent film having a two-phase morphology. What is meant by a "two-phase morphology" is that the superabsorbent component and the elastomer of the film are not compatible due to polarity and compositional differences, and therefore one component will be in a dispersed phase, as aggregations, within the other continuous component. FIG. 1 shows elastomer 12 in a dispersed phase and superabsorbent component 11 in a continuous phase. Which component is in the dispersed phase and which is in the continuous phase is typically determined by the relative percent by volume of each component.

When the elastomer has a volume percentage ranging from about 1% to 49% the elastomer is in the dispersed phase and the superabsorbent component will be in the continuous phase. Suitably the elastomer has a volume percent in the range of about 3% to 47%, more suitably in the range of about 5% to 45%, and most suitably in the range of about 10% to 40%. A dispersed phase elastomer results in a softer, less brittle superabsorbent composition having advantages in the reduction or elimination of dust, reduced or eliminated poking through the outer cover, reduced abrasion, and can form macropores through agglomeration which allows increased fluid transfer.

When the elastomer has a volume percentage over 50% the elastomer will be in the continuous phase and the superabsorbent material will be in the dispersed phase. Suitably the elastomer has a volume percent in the range of about 51% to about 90%, more suitably in the range of about 55% to about 85%, and most suitably in the range of about 60% to about 80%. A continuous phase elastomer results in a stretchable, elastomeric superabsorbent composition useful in stretchable diapers, training pants, swim pants, wound care applications, and adult incontinence garments or guards. As a stretchable elastomeric superabsorbent composition is stretched, the superabsorbent phase is exposed to body fluids which are absorbed. The higher the percentage by volume of elastomer the less absorbent material and therefore the absorption may decrease. This can be beneficial where an elastic absorbent is needed and high absorbent capacity is not required.

The two-phase superabsorbent composition embodiment in FIG. 1 is a superabsorbent film. Other embodiments of the two-phase superabsorbent composition include superabsorbent fibers, superabsorbent staple films, particulate superabsorbent, and any other form superabsorbent polymers may take.

Figure 2:
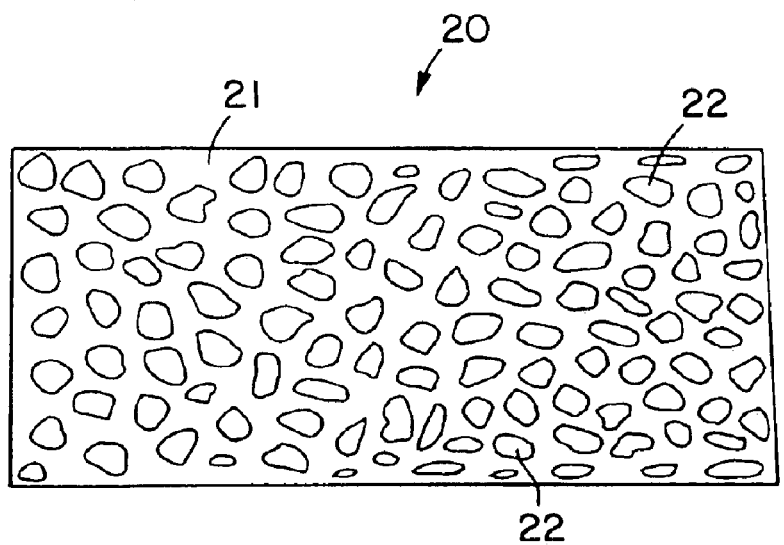
FIG. 2 is a top view of a macroporous film according to one embodiment of the invention.

FIG. 2 shows another embodiment of a superabsorbent film. Superabsorbent film 20 comprises superabsorbent component 21 and an elastomer, preferably derived from latex (not shown). The latex is an emulsion of elastomer particles (typically less than 1 micron) dispersed in water. Superabsorbent component 21 and the latex component can comprise any of the previously described embodiments. Superabsorbent 21 is not crosslinked prior to the film-making process and the latex component preferably has a low glass transition temperature. Superabsorbent film 20 comprises about 70%–90% by weight of superabsorbent component 21 and about 10%–30% by weight of latex component. As in previously described embodiments, superabsorbent component 21 forms a first continuous phase in the resulting film and the latex component forms a second dispersed phase.

Superabsorbent film 20 also comprises macropores 22. Macropores 22 refer to pores in superabsorbent film 20 having a pore diameter generally greater than about 100 μm. Suitably the pore size is between about 150 μm and about 10,000 μm, more suitably between about 1000 μm and about 6000 μm and most suitably between about 1500 μm and about 4000 μm. It is believed that macropores 22 form because of the migration of the dispersed elastomer particles after film production. The formation of macropores 22 in superabsorbent film 20 is likely caused by a various factors alone or in combination, including production conditions, surface tension of superabsorbent solutions and the latex particles, interfacial tension between the superabsorbent phase and the latex phase. Migration of latex particles towards other latex particles, thereby causing voids, is influenced by polarity and compositional differences between latex and superabsorbent.

The macropores typically form immediately after the film is cast. The pores initially start, then grow, and then stabilize. The completion of the pores usually takes several minutes at room temperature (~23° C.).

Macroporous superabsorbent film has the advantage of absorbency and improved fluid transfer. Superabsorbent film provides the advantages previously discussed and the fluid transfer through the macropores allow for production of thinner and more clothes-like absorbent garments. The use of macroporous film in absorbent articles allows the use of a 100% superabsorbent material absorbent core, thus reducing thickness by eliminating the wood pulp matrix of the typical absorbent core.

The size of macropores 22 grow upon further migration of the latex particles. In one embodiment macropores 22 grow and eventually border each other, forming a reticular structure. Suitable embodiments of the macroporous superabsorbent film have an open macropore area of about 10% to about 70%, more suitably about 20% to about 60%, and most suitably about 25% to about 50%. Suitable embodiments of the macroporous superabsorbent film have an mean pore size, as measured by equivalent circle diameter, range from about 150 μm to 10,000 μm, more suitably between about 1000 μm to 6000 μm, and most suitably between about 1500 μm to 4000 μm. Equivalent circle diameter is determined by image analysis of the microporous film as described in the examples below.

It has been surprisingly discovered that the formation of macroporous film and latex particle migration is dependent upon the percentage by dry weight of the elastomers in the dry mixture of superabsorbent precursor and elastomer. At a low level of latex, about 1.5% to 5% by dry weight for example, there is not enough volume of latex particle in superabsorbent film 20 to provide the free energy driving force for migration and there is no void formation and thus no macroporous film. At high levels of latex, about 40% or higher, the volume fraction of latex is high and the migration distance for the latex particles is not great enough to create enough energy for void initiation, resulting in a solid, non-macroporous film. It has been discovered that using an intermediate range of latex, about 8% to 35% by dry weight, the energy required for the void formation is sufficient for initiation and growth of macropores 22.

Macroporous superabsorbent film 20 can be crosslinked by curing at a temperature sufficient to cause the crosslinking between the carboxy groups on the superabsorbent precursor component and at least one of the latent hydroxy groups or amino groups on the copolymerized latent crosslinkable comonomer on the polymer chain and the polyfunctional compounds via an esterification reaction. A suitable temperature for curing is about 100° C. to 240° C., more suitably about 120° C. to 200° C., and a typical curing time is for about 20 to 40 minutes. A higher curing temperature usually requires a shorter curing time to avoid over crosslinking which can reduce absorbency values.

Curing or crosslinking can be achieved by using microwave, electron beam and other high energy methods at a lower temperature and for a shorter time.

Figure 17:
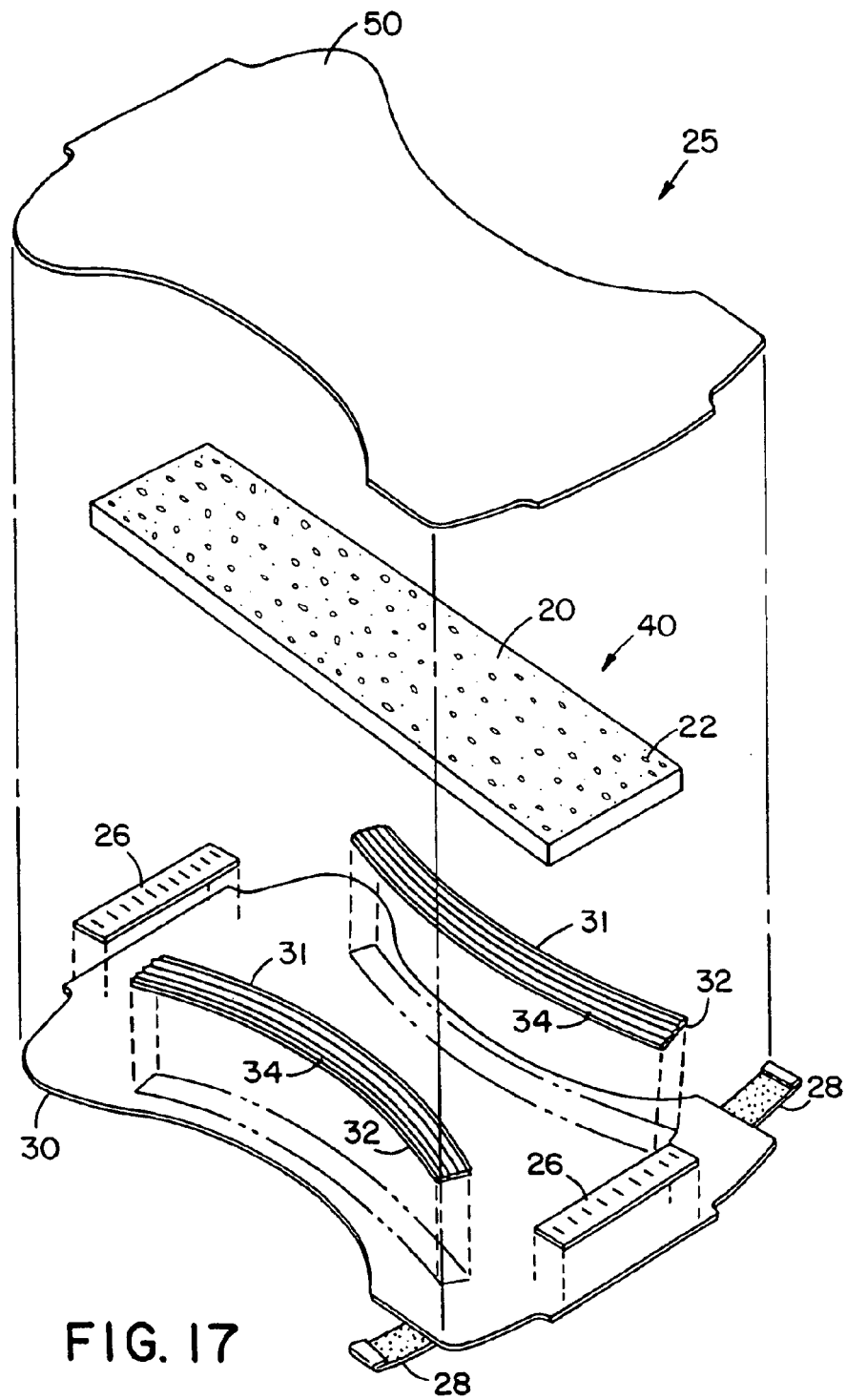
FIG. 17 is an exploded perspective view of a diaper according to one embodiment of the invention.

One preferred personal care absorbent article according to this invention is a disposable diaper. FIG. 17 illustrates an exploded perspective view of a disposable diaper according to one embodiment of the present invention. Disposable diaper 25 includes an outer cover 30, a body-side liner 50, and an absorbent composite 40 located between the body-side liner 50 and the outer cover 30. The absorbent composite 40 comprises macroporous superabsorbent film 20 in the form of a laminate with another absorbent material. Absorbent materials can include natural and wood pulp fibers and nonwoven fibers or webs. "Nonwoven" and "nonwoven web" refer to materials and webs of material which are formed without the aid of a textile weaving or knitting process. The absorbent material can also contain superabsorbent material, such as particles or fibers, within the wood pulp matrix. The superabsorbent particles or fibers in the absorbent material can be superabsorbent compositions of this invention or any other superabsorbent materials.

Attached to outer cover 30 are waist elastics 26, fastening tapes, or mechanical fasteners such as VELCRO™ hooks and loops, 28 and leg elastics 31. Fastening tapes 28 can also be mechanical fasteners such as VELCRO™ hooks and loops. The leg elastics 31 comprise a carrier sheet 32 and individual elastic strands 34.

Figure 18:
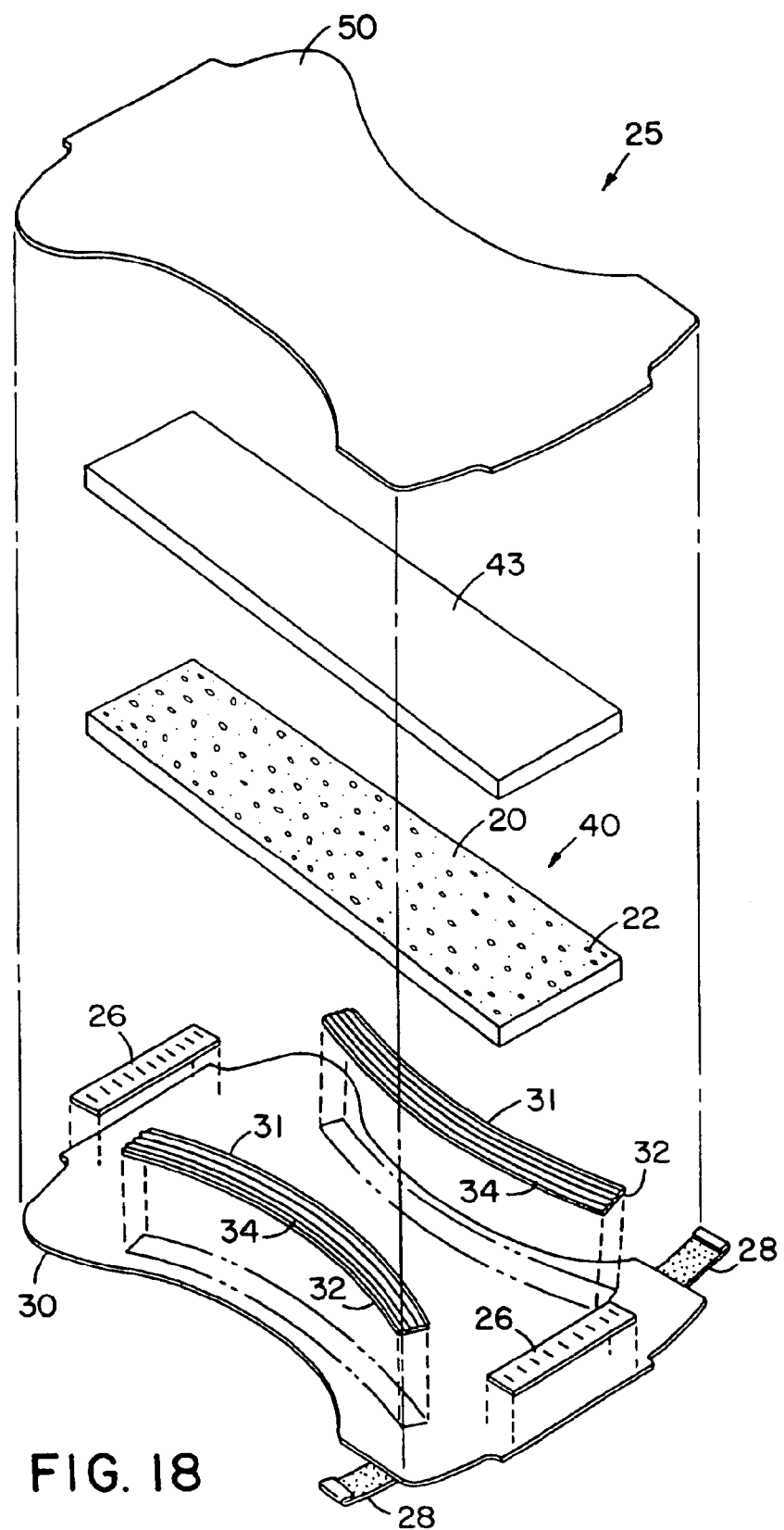
FIG. 18 is an exploded perspective view of a diaper according to another embodiment of the invention.

FIG. 18 show another embodiment of diaper 25. FIG. 18 is similar to FIG. 17 with the addition of surge layer 43 located between body-side liner 50 and absorbent composite 40. Examples of surge material useful for this invention can be found in U.S. Pat. No. 5,364,382 issued to Latimer, et al., and U.S. Pat. No. 5,490,846 issued to Ellis, both of which are hereby incorporated by reference. Surge layer 43 is made of a surge material. Surge layer 43, positioned adjacent to the body-side liner in the crotch region, regulates the flow of liquid surging into the absorbent composite. Surge layer 43 has an operable level of density and basis weight to quickly collect and temporarily hold liquid surges, to transport the liquid from its initial entrance point and to substantially completely release the liquid to pockets 50 and superabsorbent 58. The surge layer may also be above (on the outside of) the body-side liner.

The body-side liner 50, surge layer 43 and outer cover 30 are constructed of conventional non-absorbent materials. By "non-absorbent" it is meant that these materials, excluding the pockets filled with superabsorbent, have an absorptive capacity not exceeding 5 grams of 0.9% aqueous saline solution per gram of material, using the absorption test described above. Both the surge layer 43 and body-side liner 50 are constructed from highly liquid pervious materials. These layers function to transfer liquid from the wearer to the interior of the absorbent article. Suitable liquid pervious materials include porous woven materials, porous nonwoven materials, films with apertures, open-celled foams, and batting. Examples include, without limitation, any flexible porous sheets of polyolefin fibers, such as polypropylene, polyethylene or polyester fibers; webs of spunbonded polypropylene, polyethylene or polyester fibers; webs of rayon fibers; bonded carded webs of synthetic or natural fibers or combinations thereof. U.S. Pat. No. 5,904,675, issued 18 May 1999 to Laux et al. and incorporated by reference, provides further examples of suitable surge materials. Either layer may also be an apertured plastic film.

Figure 19:
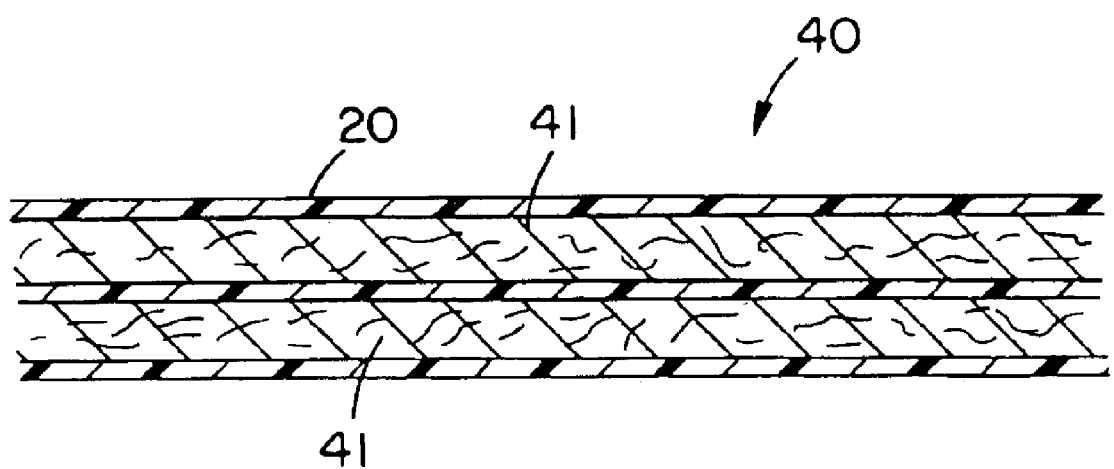
FIG. 19 is a cross-sectional view of a multi-layer laminate including the superabsorbent film of the invention.

FIG. 19 shows one embodiment of absorbent composite 40 comprising a multi-layered laminate. Absorbent composite 40 comprises two absorbent layers 41 between three macroporous superabsorbent films 20. Absorbent composite 40 can have various numbers and configurations of layers of absorbent layers 41 and macroporous superabsorbent films 20. Absorbent layers 41 can comprise at least one of natural or wood pulp fibers and a superabsorbent. Superabsorbent can be in the form of particles, staple fibers, foams, or other physical and geometrical forms or shapes. The weight percentage of the superabsorbent in the absorbent layer 41 can range from 5 to 95% by weight, or 10 to 90% by weight, or 20 to 80% by weight. In another embodiment absorbent composite 40 can comprise one macroporous superabsorbent films 20 between two absorbent layers 41 or two macroporous superabsorbent films 20 between three absorbent layers 41. More than one superabsorbent films 20 can also be layered above or below an absorbent layer 41. For example, three superabsorbent films 20 can be layered between absorbent layer 41 and outer cover 30.

The multi-layered laminate absorbent composite has advantages in increasing absorbency and allowing a thinner absorbent composite, which is desired and beneficial in personal care absorbent articles. Using superabsorbent films in absorbent composite 40 also provides strength, especially when absorbent composite 40 is wet. Superabsorbent particle in absorbent layer 41 can separate when wet and can move throughout the absorbent article and may even exit the body-side liner. A microporous superabsorbent film 20 solves this problem, as the film cannot detach from absorbent composite 40 and move within the absorbent article. It was surprisingly discovered that the microporous superabsorbent films became tacky and adhesive to the absorbent layer 41 when it was wet with a bodily fluid or saline. The wet microporous superabsorbent film was found to function as an adhesive layer or binder layer for the absorbent layer 41 to prevent the migration of the wet superabsorbent particles. This new function of the microporous superabsorbent film improved the wet integrity of the absorbent composite 40.

Superabsorbent films without macropores can be substituted as at least one layer in the multi-layered laminate. FIG. 19 shows a five layer laminate, three macroporus film layers and two absorbent layers, but the number of each type of layers can vary depending on absorbency needs.

Superabsorbent compositions of this invention are useful in absorbent articles such as facial tissue and paper towels. In one embodiment of this invention a superabsorbent film of this invention is placed between two plies of either facial tissue or paper towel. Placing a superabsorbent composition of this invention, such as a film, between two plies of a facial tissue or a paper towel, such as HI-DRY® or VIVA® or SCOTT® paper towels, available from Kimberly Clark, Inc., Neenah, Wis., increases the absorption capacity of the tissue or towel. The softness and flexibility of the superabsorbent compositions of this invention allow for the application to facial tissues and paper towels.

EXAMPLES

As previously discussed, embodiments of this invention include a broad variation of superabsorbent components and combinations of those components. To demonstrate the invention a series of superabsorbent compositions were prepared. Two different superabsorbent precursor solutions were used to make the examples, the first precursor is a 70% neutralized copolymer of acrylic acid and aminopropyl vinyl ether. The second superabsorbent precursor is a partially hydrolyzed copolymer of isobutylene and maleic anhydride, and diethylenetriamine as a latent crosslinker. For Examples 1–6, a superabsorbent precursor solution with 24% solid weight was used.

For Examples 1–6 the latex emulsion used was a styrene-butadiene copolymer emulsion, GOOD-RITE® SB 1168 available from BFGoodrich Specialty Chemicals (Cleveland, Ohio). The latex has a solid content of 56.6% by weight and 43.4% by weight water.

Example 1 was made by adding 302.51 g of a solution of 70% neutralized copolymer comprising 98% by mole of acrylic acid and 2% by mole of aminopropyl vinyl ether (collectively NPAA) and 2.03 g of SB 1168 latex emulsion. Due to the presence of water in both the superabsorbent solution and the latex emulsion the resulting dry weight of the NPAA was 72.6 g and the dry weight of the elastomer derived from latex emulsion was 1.15 g (equaling 1.5% by weight elastomer). The components were mixed in a Hobart mixer at setting #1 for 5 minutes to obtain a uniform mixture for film production. Examples 2–6 were made by the same procedure as Example 1 except that the actual weight percentage of the NPAA and the latex were different. The weights of the components of each example are listed in Table 1. A control film (Control) was also made from a NPAA superabsorbent precursor having no latex.

TABLE 1

| Example No. | NPAA Weight (g) | Elastomer Weight (g) | Elastomer (wt. %) |
|---|---|---|---|
| Example 1 | 302.51 | 2.03 | 1.5 |
| Example 2 | 303.14 | 7.29 | 5 |
| Example 3 | 303.71 | 14.26 | 10 |
| Example 4 | 309.27 | 31.93 | 20 |
| Example 5 | 307.01 | 54.65 | 30 |
| Example 6 | 307.32 | 85.20 | 40 |

The above superabsorbent compositions and the Control were made into superabsorbent particles by drying at 60° C. overnight, grinding the dried solid superabsorbent composition, and curing the composition at 120° C. for 4 hours. The particles of Examples 1–6 were found to have significantly reduced hardness and rigidity as compared to the Control. The reduced hardness and rigidity of the particles are beneficial in both the manufacture and the use of absorbent articles.

Examples 1–6 were made into thin films using an ACCU-LAB™ drawdown machine by Industry Tech (Oldsmar, Fla.). The film thickness was controlled the wire size on the steel bar. A sheet of BYTAC VF-81 Chemical Resistant TEFLON FEP® film from Norton Performance Plastics (Akron, Ohio) was adhered to the glass plate of the drawdown machine. A solution of about 2 grams of each of Examples 1–6 was made into a film. The films were allowed to dry and the film compositions and thicknesses are summarized in Table 2.

TABLE 2

| Example No. | Film Composition (approx. dry weight ratio) | Film Thickness (inch) | Macroporous |
|---|---|---|---|
| Example 1 | 1.5% Elastomer/98.5% NPAA | 0.004 | No |
| Example 2 | 5% Elastomer/95% NPAA | 0.003 | No |
| Example 3 | 10% Elastomer/90% NPAA | 0.004 | Yes |
| Example 4 | 20% Elastomer/80% NPAA | 0.003 | Yes |
| Example 5 | 30% Elastomer/70% NPAA | 0.003 | Yes |
| Example 6 | 40% Elastomer/60% NPAA | 0.004 | No |

Figure 7:
FIG. 7 is a photograph of a top view of a superabsorbent film according to one embodiment of this invention.
Figure 8:
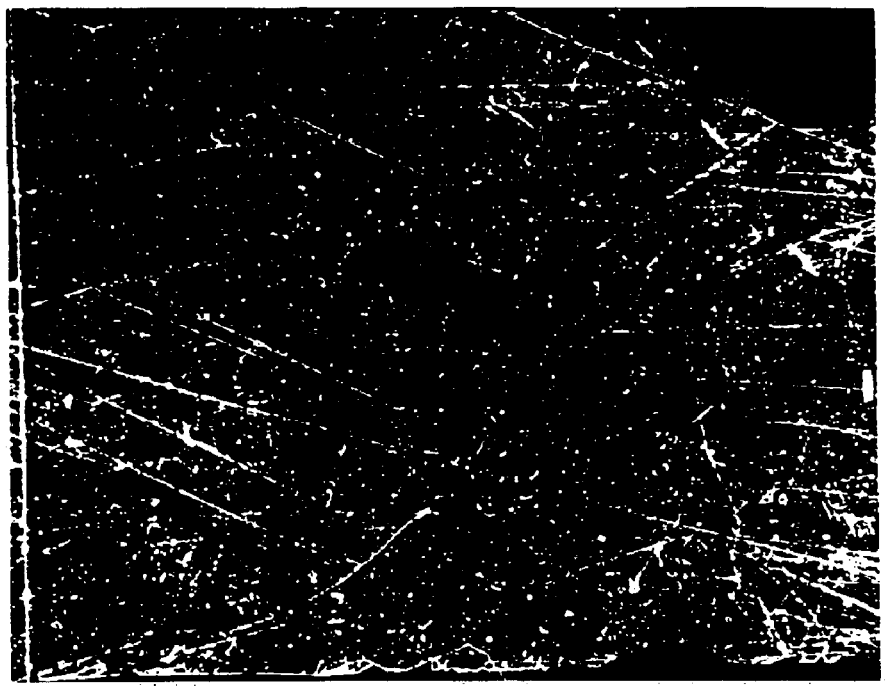
FIG. 8 is a photograph of a top view of a superabsorbent film according to one embodiment of this invention.
Figure 9:
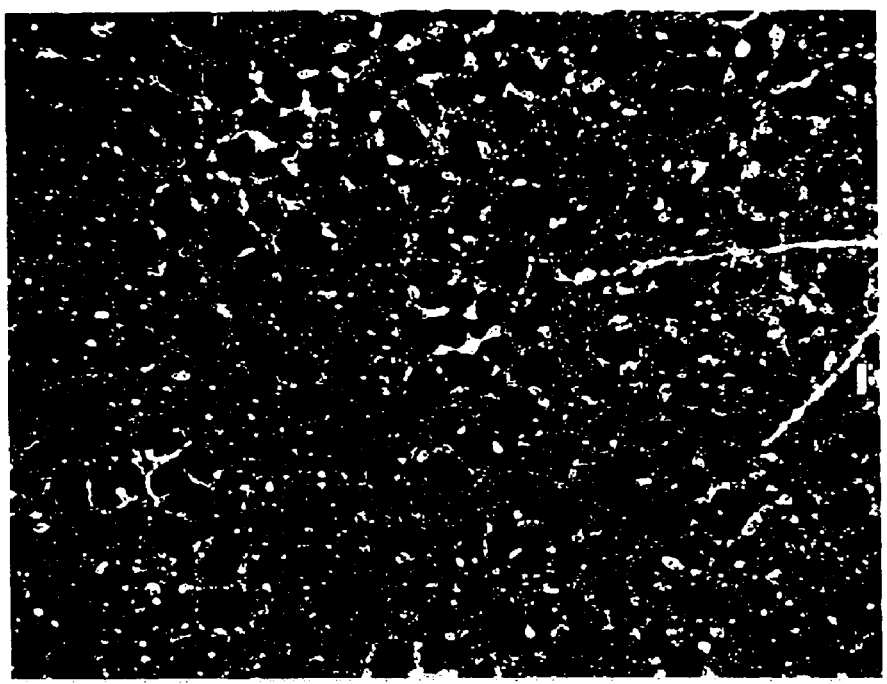
FIG. 9 is a photograph of a top view of a superabsorbent film according to one embodiment of this invention.
Figure 10:
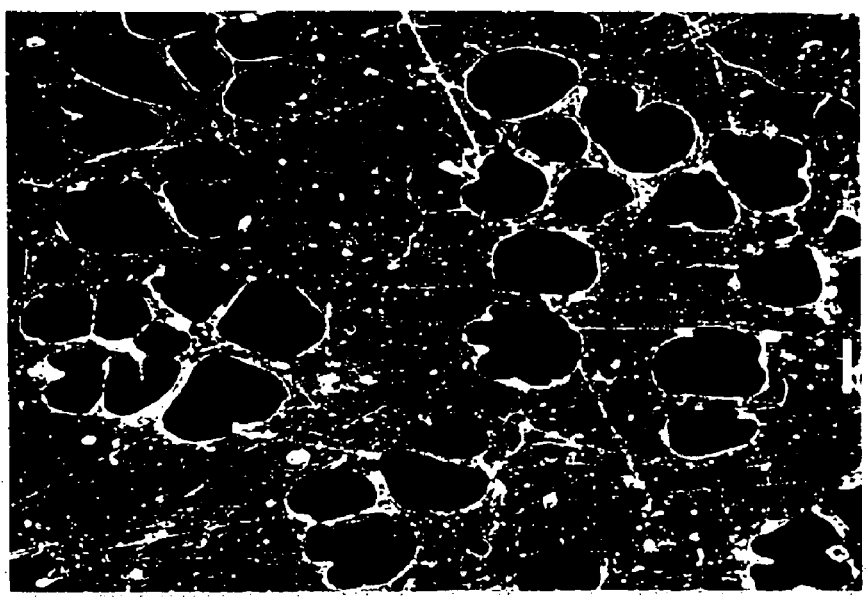
FIG. 10 is a photograph of a top view of a superabsorbent film according to one embodiment of this invention.
Figure 11:
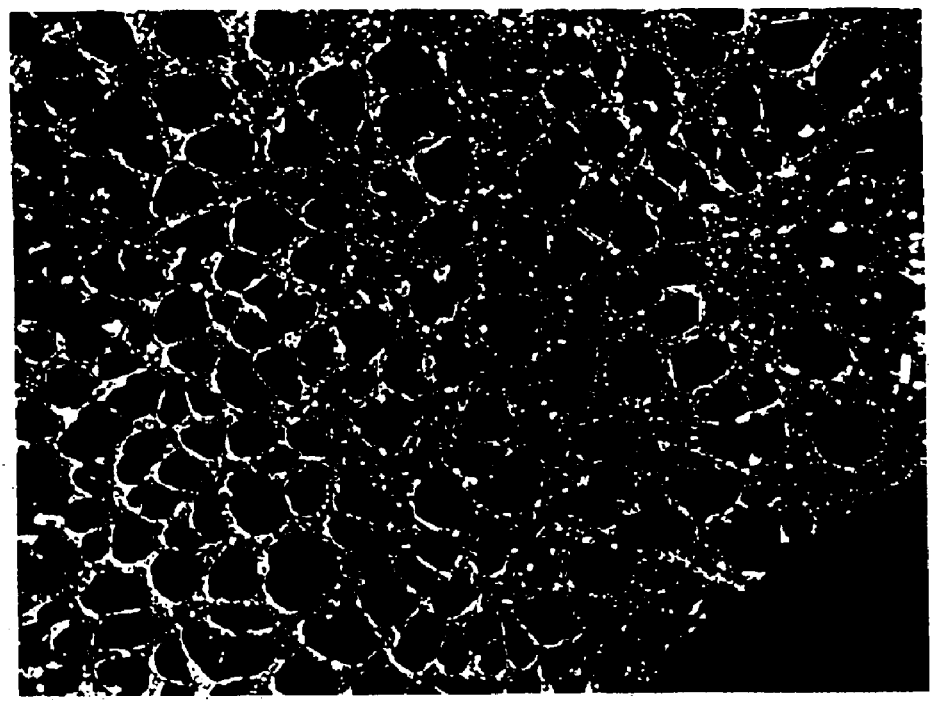
FIG. 11 is a photograph of a top view of a superabsorbent film according to one embodiment of this invention.
Figure 12:
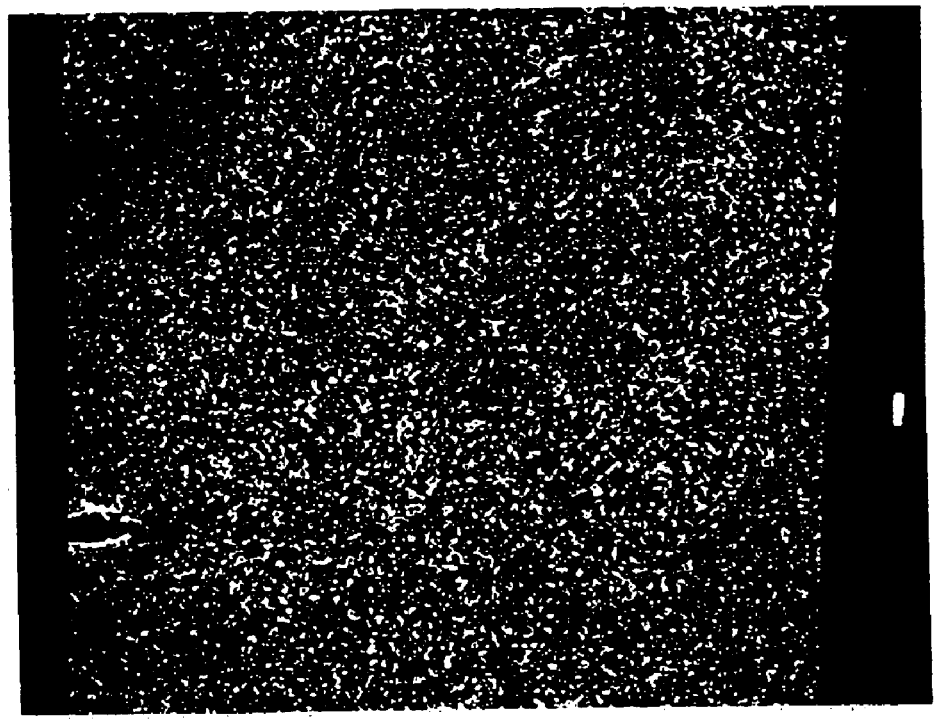
FIG. 12 is a photograph of a top view of a superabsorbent film according to one embodiment of this invention.

FIGS. 7–12 are photographs of the films of Examples 1–6 taken at a magnification of 3.8 times. FIG. 7 (Example 1), FIG. 8 (Example 2), and FIG. 12 (Example 6) show films not having macropores. FIG. 9 (Example 3), FIG. 10 (Example 4), and FIG. 11 (Example 5) all show films having macropores as described in this Patent Application.

Figure 5:
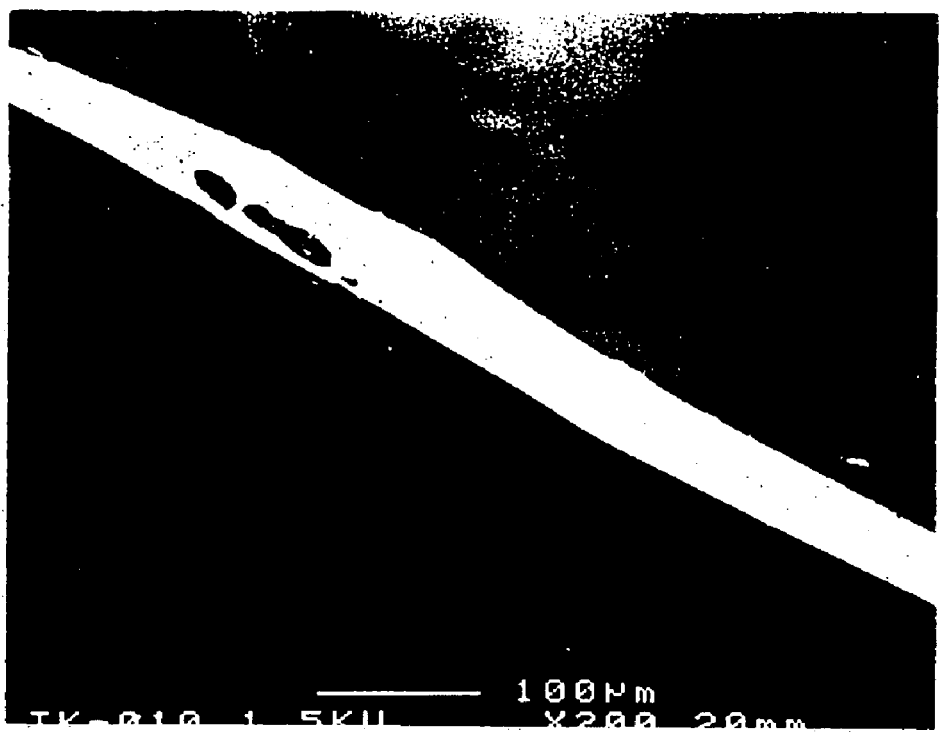
FIG. 5 is a photograph of a sectional view of a superabsorbent film according to one embodiment of the invention.
Figure 6:
FIG. 6 is a photograph of a sectional view of a superabsorbent film according to one embodiment of the invention.
Figure 6:

The fractured edges of the films were stained with osmium tetroxide which reacts with unsaturated carbon double bonds present in the latex phase. The morphology of the films was then analyzed by scanning electron microscopy (SEM). SEM analysis of the stained edges was performed using a low electron accelerating voltage (1.5 kiloelectron volts) and a micro-channel plate backscatter electron (BEI) detector was used to collect the SEM BEI images. FIGS. 5 and 6 are sectional photographs of the film of Example 3. FIG. 5 is magnified 200 times and FIG. 6 is magnified 1000 times.

The osmium tetroxide stains the latex particles and the SEM analysis shows the latex aggregates form an "islands-in-the-sea" type blend morphology as shown in FIGS. 5 and 6. The lighter regions comprise the stained elastomer component derived from latex. The elastomer exists as a dispersed phase in the superabsorbent composition which can be easily seen in a photograph. Superabsorbent component 11 and elastomer derived from latex component 12 were separated in a two-phase morphology resulting from the non-compatibility of the two components. Elastomer derived from latex aggregation was most prevalent in Examples 3–5. In Examples 1 and 2 the latex percentages are lower and there was not enough volume of elastomer particle in the composition to provide the free energy driving force for migration.

The size of the elastomer aggregates in Examples 3–5 varied, ranging from about 1 μm to about 90 μm in the film surface dimension. There were many small elastomer aggregates in all Examples, ranging from about 3 μm to about 7 μm. The large elastomer aggregates ranged from about 50 μm to about 90 μm in the film surface dimension. In Example 3 the largest elastomer aggregates ranged from about 50 μm to about 70 μm in the film surface dimension and about 10 μm to about 20 μm in the film thickness dimension. In Example 5 the largest elastomer aggregates ranged from about 70 μm to about 90 μm in the film surface dimension and about 20 μm to about 40 μm in the film thickness dimension.

The glass transition temperature for the Control film and Examples 3–6 were determined by differential scanning calorimetry (DSC) on a TA Instrument 2920 calorimeter. The samples were dried under vacuum, about 27 inches mercury at 70° C., for two days. Thermograms were obtained under a dynamic nitrogen atmosphere in the range from −100° C. to 150° C. and at a heating rate of 10° C./min. The measured glass transition temperatures are summarized and shown in Table 3.

TABLE 3

| Example No. | Glass Transition Temperature (° C.) |
|---|---|
| Control | 45; 110 |
| Example 3 | −28; 46; 111 |
| Example 4 | −29; 52; 126 |
| Example 5 | −29; 75; 128 |
| Example 6 | −29; 67; 106 |

The Control film had glass transition temperatures above room temperature. In addition to the glass transition temperature above room temperature (45° C. and 111° C.), the superabsorbent compositions of this invention had an additional glass transition temperatures of about −28° C. to about −29° C. due to the elastomer phase present in the superabsorbent compositions, which is more than 50° C. lower than room temperature. The low glass transition temperature superabsorbent compositions of this invention have improved impact properties, improved flexibility, more durability, and increased softness are making them desirable in personal care products.

Superabsorbent films produced using Examples 1, 2, and 6 were solid films with no macropores. Film made from Examples 3–5 formed macropores. The pore size and pore size distribution of the resulting macroporous films were determined by image analysis. Image analysis can be done using a Quantimet 600 IA System, available from Leica, Inc., Cambridge, United Kingdom. A customized IAS program routine was written ("PORES3") implementing the systems software (QWIN version 1.06) and used in the analysis. Optical configuration included a Dage 81 camera, a 40 mm Ei-Nikkor lens, light transmitted through a collimated light box, and a ⅛ inch glass cover plate. The data were acquired from a minimum of four fields-of-view. The results obtained from the image analysis are listed in Table 4.

TABLE 4

| Example No. | Mean Equivalent Circular Diameter (μm) | Standard Deviation (μm) | Standard Error (μm) | Open Area (%) |
|---|---|---|---|---|
| Example 3 | 2136 | 1480 | 133 | 27.7 |
| Example 4 | 1852 | 675 | 46 | 48.5 |
| Example 5 | 1507 | 596 | 46 | 27.5 |

Figure 3:
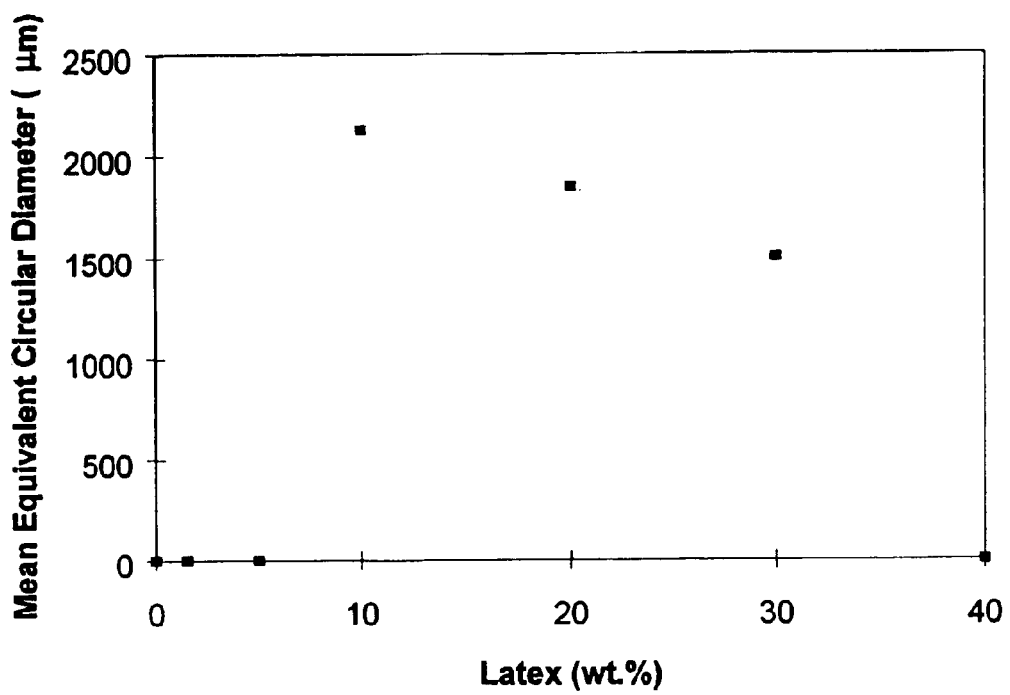
FIG. 3 is a graph plotting the mean equivalent circular diameter of the macropores against the latex weight percent.
Figure 4:
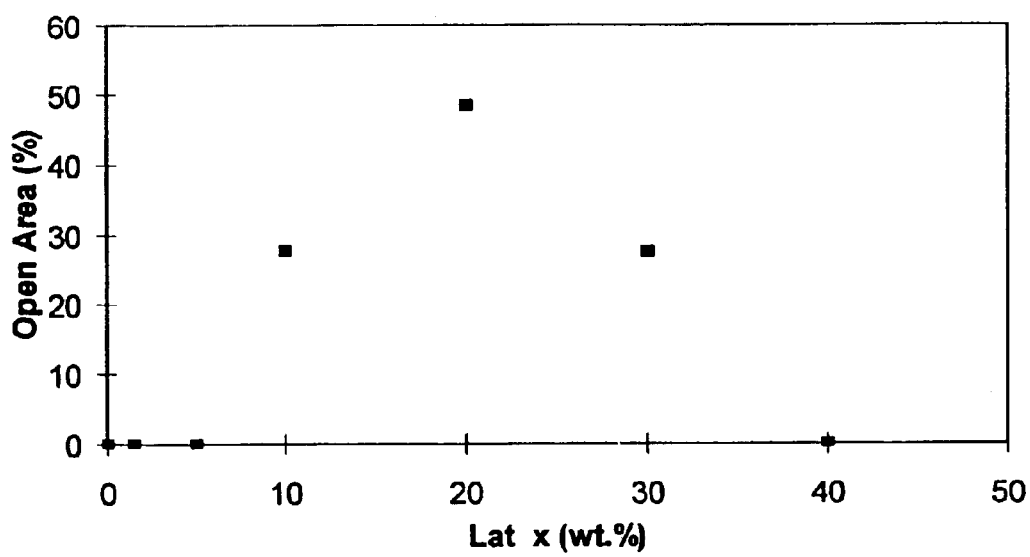
FIG. 4 is a graph plotting the macropore open area (%) against the latex weight percent.

The results of the image analysis summarized in Table 4 show that the mean diameter of the macropores 22 in the films, as measured by equivalent circular diameter (ECD), depends on the weight percentage of the latex in the superabsorbent composition 20. Within the range of latex percentage that causes macropore formation, the mean macropore size decreases with the increase of the amount of latex in the film. This allows pore size to be controlled. FIG. 3 is a graph plotting the mean equivalent circular diameter of Examples 1–6 against the weight percentage of latex in each sample. FIG. 4 is a graph plotting the open area (%) of Examples 1–6 against the weight percentage of latex in each sample.

Macropore size distribution is summarized in Table 5.

TABLE 5

| Bin | ECD (μm) | Example 3 Count | Example 3 % Count | Example 4 Count | Example 4 % Count | Example 5 Count | Example 5 % Count |
|---|---|---|---|---|---|---|---|
| 1 | 10.0–15.8 | 0 | 0.00 | 0 | 0.00 | 0 | 0.00 |
| 2 | 15.8–25.1 | 0 | 0.00 | 0 | 0.00 | 0 | 0.00 |
| 3 | 25.1–39.8 | 0 | 0.00 | 0 | 0.00 | 0 | 0.00 |
| 4 | 39.8–63.1 | 0 | 0.00 | 0 | 0.00 | 0 | 0.00 |
| 5 | 63.1–100 | 1 | 0.88 | 0 | 0.00 | 0 | 0.00 |
| 6 | 100–158 | 3 | 2.44 | 0 | 0.00 | 1 | 0.60 |
| 7 | 158–251 | 6 | 4.88 | 2 | 0.93 | 0 | 0.00 |
| 8 | 251–398 | 16 | 13.1 | 3 | 1.39 | 1 | 0.60 |
| 9 | 398–631 | 7 | 5.69 | 7 | 3.24 | 2 | 1.19 |
| 10 | 631–1000 | 9 | 7.32 | 13 | 6.02 | 9 | 5.36 |
| 11 | 1000–1585 | 10 | 8.13 | 43 | 19.91 | 94 | 55.95 |
| 12 | 1585–2512 | 12 | 9.76 | 120 | 55.56 | 59 | 35.12 |
| 13 | 2512–3981 | 47 | 38.21 | 27 | 12.5 | 1 | 0.60 |
| 14 | 3981–6310 | 12 | 9.76 | 1 | 0.46 | 0 | 0.00 |
| 15 | 6310–10000 | 0 | 0.00 | 0 | 0.00 | 1 | 0.60 |

Additional Examples 7–9 were made by the same procedure of Example 1, except that the actual weight percentage of the superabsorbent material and the latex were different and the superabsorbent material was a 55% neutralized isobutylene-maleic anhydride. Examples 7–9 were also cast into films. Example 2–6 and the Control were cured at 180° C. for 40 minutes, Examples 7–9 were cured at 160° C. for 120 minutes. The absorbency of the cured films for Examples 2–9 were measured under zero load (AUZL) and under load (AUL) at 0.3 psi (pounds per square inch). The results are an average of two repetitions and summarized in Table 6. The film of Example 3 was also cured at 180° C. for 60 minutes and had an average absorbency under zero load (AUZL) value of 16.5 g/g and an absorbency under load (AUL) at 0.3 psi of 12.7 g/g of 0.9% by weight NaCl solution. Again, these results are an average of two repetitions.

TABLE 6

| Example No. | AUZL (g/g) | 0.3 psi AUL (g/g) |
|---|---|---|
| Control | 15.0 | 12.6 |
| 2 | 12.4 | 10.6 |
| 3 | 13.2 | 11.1 |
| 4 | 14.4 | 11.2 |
| 5 | 12.9 | 10.3 |
| 6 | 9.4 | 7.9 |
| 7 | 30.1 | 18.5 |
| 8 | 30.7 | 12.0 |
| 9 | 24.2 | 10.7 |

(Absorbent test was done in 0.9% by weight NaCl solution)

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

We claim:

1. A superabsorbent composition, comprising:
    a superabsorbent material having a glass transition temperature higher than the temperature of use; and
    an elastomer having a glass transition temperature lower than the temperature of use;
    the superabsorbent material and the elastomer are in a two-phase superabsorbent composition wherein the superabsorbent material is in a first phase and the elastomer is in a second phase.

2. The superabsorbent composition of claim 1, wherein the superabsorbent material comprises a cross-linked partially neutralized polyacrylic acid.

3. The superabsorbent composition of claim 1, wherein the first phase superabsorbent material is a continuous phase and the second phase elastomer is a dispersed phase.

4. The superabsorbent composition of claim 1, wherein the first phase superabsorbent material is a dispersed phase and the second phase elastomer is a continuous phase.

5. The superabsorbent composition of claim 1, wherein the superabsorbent material is derived from a precursor solution comprising a copolymer containing a latent crosslinker.

6. The superabsorbent composition of claim 5, wherein the latent crosslinker ranges from 1 to 8% by weight.

7. The superabsorbent composition of claim 5, wherein the latent crosslinker ranges from 2 to 6% by weight.

8. The superabsorbent composition of claim 5, wherein the latent polymerizable crosslinker comprises a comonomer selected from α,β-ethylenically unsaturated comonomers having an additional functional group capable of reacting with carboxyl groups.

9. The superabsorbent composition of claim 8, wherein the latent polymerizable crosslinker comprises a comonomer selected from aminopropyl vinyl ether, ethylene glycol allyl ether, 2-hydroxyethyl methacrylate, and ethylene glycol vinyl ether.

10. The superabsorbent composition of claim 5, wherein the copolymer comprises acrylic acid and a polymerizable crosslinker.

11. The superabsorbent composition of claim 1, wherein the superabsorbent material is derived from a precursor solution comprising a superabsorbent precursor and a nonpolymerizable crosslinker.

12. The superabsorbent composition of claim 11, wherein the nonpolymerizable crosslinker comprises a compound selected from the group consisting of ethylene glycol, diethylene glycol, triethylene glycol, polyethelene glycol, polyvinyl alcohol, polyethylele oxide, glycerol, 1,3-propanediol, 1,4-butanediol, 1,5-pentanediol, 1,6-hexanediol, 1,8-octanediol, 1,1,1-trimethylolpropane, 1,4-butanediamine, 1,5-pentanediamine, 1,6-hexanediamine, diethylenetriamine, and analogs and derivatives thereof.

13. The superabsorbent composition of claim 12, wherein the nonpolymerizable crosslinker comprises a compound having at least 2 functional groups capable of reacting with carboxyl groups.

14. The superabsorbent composition of claim 11, wherein the nonpolymerizable crosslinker ranges from 1 to 8% by weight.

15. The superabsorbent composition of claim 11, wherein the nonpolymerizable crosslinker ranges from 2 to 6% by weight.

16. The superabsorbent composition of claim 1, the superabsorbent material further comprising a crosslinked and partially hydrolyzed copolymer of an α-olefin with one of an α,β-ethylenically unsaturated organic acid anhydride and ester.

17. The superabsorbent composition of claim 16, wherein the crosslinked and partially hydrolyzed copolymer of an α-olefin with one of an α,β-ethylenically unsaturated organic acid anhydride and ester comprises a crosslinked and partially hydrolyzed copolymer of isobutylene and maleic anhydride.

18. The superabsorbent composition of claim 16, wherein the superabsorbent material is derived from a partially hydrolyzed copolymer of an α-olefin with one of an α,β-ethylenically unsaturated organic acid anhydride and ester and a nonpolymerizable latent crosslinker.

19. The superabsorbent composition of claim 18, wherein the superabsorbent material is derived from a partially hydrolyzed copolymer of isobutylene and maleic anhydride and a nonpolymerizable latent crosslinker.

20. The superabsorbent composition of claim 1, wherein the superabsorbent material comprises one of the group consisting of hydrolyzed starch-acrylonitrile graft copolymers, partially neutralized starch-acrylonitrile graft copolymers, partially neutralized saponified vinyl-acetate acryl-ester copolymers, hydrolyzed acronitrile copolymers, carboxymethyl cellulose, carboxymethyl starch, chitosan salts, partially neutralized polyaspartic acid, polyquartemary ammonium salts, polyvinyl amines, polyvinyl imines, and combinations thereof.

21. The superabsorbent composition of claim 1, wherein the elastomer is derived from a latex emulsion.

22. The superabsorbent composition of claim 1, wherein the elastomer has a glass transition temperature below room temperature.

23. The superabsorbent composition of claim 1, wherein the elastomer has a glass transition temperature less than about 25° C.

24. The superabsorbent composition of claim 1, wherein the elastomer has a glass transition temperature less than about 0° C.

25. The superabsorbent composition of claim 1, wherein the elastomer has a glass transition temperature less than about −25° C.

26. The superabsorbent composition of claim 1, wherein the superabsorbent composition comprises a film.

27. The superabsorbent composition of claim 1, wherein the superabsorbent composition comprises a particle.

28. The superabsorbent composition of claim 27, wherein the particle has a size of 50 to 1,000 microns.

29. The superabsorbent composition of claim 27, wherein the particle has a size of 150 to 800 microns.

30. The superabsorbent composition of claim 1, wherein the superabsorbent composition comprises a fiber.

31. The superabsorbent composition of claim 30, wherein the fiber has a diameter of 0.1 to 100 microns.

32. The superabsorbent composition of claim 30, wherein the fiber has a diameter of 1 to 70 microns.

33. The superabsorbent composition of claim 30, wherein the fiber has a diameter of 5 to 50 microns.

34. A personal care absorbent article comprising the superabsorbent composition of claim 1.

35. A protective garment comprising the superabsorbent composition of claim 1.

36. The film of claim 37, wherein the elastomer has a glass transition temperature below about 25° C.

37. A method for producing the superabsorbent composition of claim 1, the method comprising:
   mixing a superabsorbent precursor and a latex emulsion to form a mixture including a dispersed elastomer phase and a continuous superabsorbent phase;
   forming a composition from the mixture;
   drying the composition; and
   crosslinking the composition by one of heat curing, electron beam, microwave, and combinations thereof.

* * * * *